United States Patent
Engel et al.

[11] Patent Number: 5,942,639
[45] Date of Patent: Aug. 24, 1999

[54] PROCESS FOR THE PREPARATION OF ALKYLPHOSPHOCHOLINES AND THE PRODUCTION THEREOF IN PURE FORM

[75] Inventors: Jürgen Engel, Alzenau; Bernd Kutscher, Maintal; Wolfgang Schumacher, Langen; Ulf Niemeyer, Offenbach; Alfred Olbrich, Obertschausen; Gerhard Nssner, Offenbach, all of Germany

[73] Assignee: Asta Medica Aktiengesellschaft, Frankfurt, Germany

[21] Appl. No.: 08/938,331

[22] Filed: Sep. 25, 1997

Related U.S. Application Data

[63] Continuation-in-part of application No. 07/905,817, Jun. 29, 1992, abandoned.

[30] Foreign Application Priority Data

Jul. 4, 1991 [DE] Germany .................................. 4122127

[51] Int. Cl.$^6$ .......................................................... C07F 9/10
[52] U.S. Cl. ............................................ 558/146; 558/166
[58] Field of Search ................................................ 558/146

[56] References Cited

U.S. PATENT DOCUMENTS 4,130,571 12/1978 Nakajima et al. ...................... 554/82
4,492,659 1/1985 Bosies et al. .......................... 558/169

*Primary Examiner*—Michael G. Ambrose
*Attorney, Agent, or Firm*—Pillsbury Madison & Sutro LLP

[57] ABSTRACT

A process for the preparation of $C_{14}$–$C_{18}$–alkylphosphocholines by reacting an n-alkanol with a chain length of $C_{14}$–$C_{18}$ with phosphorus oxychloride in an inert solvent or also without solvent in the presence or absence of a basic substance in a single vessel process and subsequent reaction of the reaction product in an inert solvent with a choline salt in the presence of a basic substance to form phosphoric acid diester chloride, subsequent hydrolysis and isolation of alkylphosphocholine as well as optionally purification using a mixed-bed ion exchanger or in successive steps with an acid ion exchanger and a basic ion exchanger.

11 Claims, No Drawings

PROCESS FOR THE PREPARATION OF ALKYLPHOSPHOCHOLINES AND THE PRODUCTION THEREOF IN PURE FORM

This is a continuation-in-part (CIP) of application Ser. No. 07/905,817, filed on Jun. 29, 1992, now abandoned.

The present invention relates to a process for the preparation of alkylphosphocholines, in a two step process, without intermediate isolation or purification.

BACKGROUND OF THE INVENTION

Eibl et al. (European Patent 225,608) describe the preparation and use of alkylphosphocholines for the treatment of tumors.

The starting material used in the Eibl process are the corresponding n-alcohol and phosphorus oxychloride. They are reacted in tetrahydrofuran to produce the phosphoric acid ester dichloride.

In a second step, 2-aminoethanol is reacted with the phosphoric acid ester dichloride to form the 2-hexadecyl-1,3,2-oxaphospholan-2-oxide in dioxane. Hydrolysis with 2N hydrochloric acid yields the open-chain amine which is exhaustively methylated to alkylphosphocholine line with dimethyl sulphate in 2-propanol.

This process has the following disadvantages: it is necessary to isolate and purify the intermediate products. In addition, alkylating reagents are used. The use of potassium carbonate as an auxiliary base in this step of the process leads to the product having a potassium content that is undesirably high for pharmaceutical purposes.

Long-chain alkylphosphocholines having an antimicrobial effect are described by Kanetani et al., Nippon Kayaku Kaushi, 9, 1452 (1984).

They are prepared using the following process: ethylene glycol and phosphorus trichloride are reacted to form 2-chloro-1,3,2-dioxaphospholane, the product is purified by distillation and is oxidized with oxygen to form 2-chloro-1,3,2-dioxaphospholane-2-oxide and then distilled again. The 2-chloro-1,3,2-dioxaphospholane-2-oxide is then reacted with 1-hexadecanol to 2-hexadecyl-1,3,2-dioxaphospholane-2-oxide. The 2-hexadecyl-1,3,2-dioxaphospholane-2-oxide is reacted with trimethylamine in an autoclave to hexadecylphosphocholine, the crude product is purified both with alkaline and with acid ion exchangers and then it is recrystallized from acetone/chloroform. The analogous process is also used to prepare the octyl-,decyl-, dodecyl, tetradecyl and octadecyl derivatives.

The disadvantage of this process is that it is necessary to work with increased pressure in the last step of the process and that the use of trimethyl amine constitutes an industrial hygiene problem. It is also a disadvantage that the hydrolysis-sensitive intermediate products 2-chloro-1,3,2-dioxaphospholane, 2-chloro-1,3,2-dioxaphospholane-2-oxide and 2-hexadecyl-2-oxa- 1,3,2-dioxaphospholane need to be isolated and purified. In addition, environmentally-undesirable solvents such as benzene are used, the solvents being changed from step-to-step.

All known processes use chromatographic methods for working up and purifying the crude products. However, chromatographic working up processes of this kind have the following disadvantages:

- their conversion to an industrial scale causes difficulties since the dimensions of the stationary phase cannot be increased at will,
- chromatographic processes are time-consuming.

SUMMARY OF THE INVENTION

The invention relates to a new, advantageous method of preparing and working up alkylphosphocholines which minimizes these difficulties.

It has surprisingly been found that the process of the present invention achieves a higher total yield, despite the use of one less purification step than in previously known processes. In addition, the present invention uses less solvent.

The process of the present invention also avoids the use of alkylating reagents such as dimethyl sulphate which lead to a high potassium content of the product due to the use of potassium carbonate as an auxiliary base. The potassium content must be kept as low as possible in substances intended for use as pharmaceutically-active substances.

The process of the present invention avoids the time-consuming chromatographic step during working up. The product purity achieved in the process claimed is greater than in the known processes.

These and other objects are achieved in a process for the preparation of $C_{14}$–$C_{18}$-alkylphospho-cholines by reacting an n-alkanol with phosphorus oxychloride and a choline salt. In the process of the present invention, an n-alkanol with a chain length of $C_{14}$–$C_{18}$ is reacted with phosphorus oxychloride in an inert solvent, or without a solvent in the presence or absence of a basic substance in a single vessel process. The product obtained is further reacted, without having been isolated and purified, in an inert solvent with a choline salt in the presence of a basic substance to form the phosphoric acid diester chloride, the alkylphosphocholine then being liberated and isolated by subsequent hydrolysis.

The first step in the conversion consists in the reaction of phosphorus oxychloride with an n-alkanol having a chain length of 14–18 hydrogen atoms. If a solvent is used, it may be a halogenated hydrocarbon, a saturated cyclic ether, an acyclic ether, a saturated hydrocarbon which contains 5 to 10 carbon atoms, a liquid aromatic hydrocarbon which can also be substituted by halogen (in particular chlorine) or in a mixture of the above-mentioned solvents. However, a solvent is not required. Optionally this step may be carried out in the presence of a basic substance conventionally used for this purpose.

Halogenated hydrocarbons that may for example be used are hydrocarbons of 1 to 6 carbon atoms, where one or several or all of the hydrogen atoms are replaced by chlorine atoms. It is for example possible to use methylene chloride, chloroform, ethylene chloride, chlorobenzene, dichlorobenzene. When halogen-substituted aromatic hydrocarbons are used, these are preferably substituted with 1 or 2 halogen atoms.

Saturated cyclic ethers that may be used are for example ethers with a ring size of 5–6 which consist of carbon atoms and 1 or 2 oxygen atoms. Examples of these solvents are tetrahydrofuran and dioxane.

The acyclic ethers may have 2 to 8 carbon atoms and are liquid. Examples that may be considered include diethylether, diisobutylether, methyl-tert.-butylether, diisopropyl ether.

Saturated hydrocarbons that may be considered are unbranched and branched hydrocarbons that contain 5 to 10 carbon atoms and are liquid. Examples that may be considered are pentane, hexane, heptane, cyclohexane.

Aromatic hydrocarbons that may for example be considered are benzene and alkyl-substituted benzenes where the alkyl substituents contain 1 to 5 carbon atoms.

Basic substances that may be considered both for the reaction of the phosphorus oxychloride with the n-alkanol and also for the subsequent reaction with the choline salt are amines, for example aliphatic amines of the formula $NR_1R_2R_3$, where $R_1$, $R_2$ and $R_3$ are the same or different and represent hydrogen or $C_1$–$C_6$-alkyl, aromatic amines such as pyridine, picoline, quinoline.

During the reaction with the choline salt, it is possible to use the basic substance required for that step at the same time with the choline salt or also before the choline salt. For the reaction with the choline salt, a solvent is needed in any case; in other words, if the first reaction step is conducted without a particular solvent, one has to be added at this stage. The molar ratio of phosphorus oxychloride to the alkanol is for example between 1,5:1 to 1:1.1.

The choline salt is for example used in excess in relation to the alkanol (about 1.1–1.5 molar excess). If the reaction of the phosphorus oxychloride with the alkanol is carried out in the presence of a basic substance, the amount of the basic substance is for example 1 to 3 Moles for each mole of $POCl_3$.

For the subsequent reaction with the choline salt the amount of basic substance used is for example 1 to 5 moles for each 1 mole of alkanol.

The reaction temperature for the reaction of phosphorus oxychloride with n-alkanol is between −30° C. and +30° C., preferably −15° C. and +5° C., in particular −10° C. and −5° C.

The reaction time for this conversion is for example 0.5–5 hours, preferably 1–3 hours, in particular 1.5–2 hours. If the reaction occurs in the presence of a basic substance, it is generally quick (about 30 minutes).

The choline salt is then added in portions or in its entirety.

Salts of choline that may for example be used are salts with mineral acids (such as sulphuric acid, hydrochloric acid), and also salts of choline with organic acids such as acetic acid, para-toluenesulphonic acid and the like.

This reaction step is carried out in an inert solvent. Solvents that may be considered for this step are the same as are used to react the phosphorus oxychloride with the n-alkanol, if this reaction occurs in a solvent.

The basic substance is then dissolved in one of the stated solvents or added dropwise without solvent.

The following are preferably used as solvent for the basic substance: halogenated hydrocarbons, saturated cyclic ethers, acyclic ethers, saturated hydrocarbons with 5 to 10 carbon atoms, liquid aromatic hydrocarbons or mixtures of these solvents. These are the same solvents that may be used for the reaction of phosphorus oxychloride with the n-alkanol.

Addition of the basic substance causes the temperature to rise. Care must be taken that the temperature is maintained within a range between 0° C. to 40° C., preferably 10° C. to 30° C., in particular at 15° C. to 20° C.

The reaction mixture is stirred at 5° C. to 30° C., preferably 15° C. and 25° C. (for example 1 hour to 40 hours, preferably 3 hours to 15 hours).

The hydrolysis of the reaction mixture is brought about by the addition of water, it being necessary to maintain a temperature between 10° C. and 30° C., preferably 15° C. and 30° C., in particular between 15° C. and 20° C.

The previously mentioned hydrolysis liquids can also contain basic substances. Basic substances that may be considered include carbonates and hydrogen carbonates of the alkaline and alkaline earth metals.

To complete the hydrolysis, the mixture is then stirred for a further 0.5 hours to 4 hours, preferably 1 to 3 hours, in particular 1.5 to 2.5 hours at 10° C. to 30° C., preferably at 15° C. to 25° C., in particular at 18° C. to 22° C.

The reaction solution is then washed with a mixture of water and alcohols (preferably aliphatically saturated alcohols with 1 to 4 carbon atoms) which may optionally also contain a basic substance.

The mixing ratio water:alcohol may for example be between 5 and 0.5, preferably 1–3 (V/V).

Basic substances which may be considered as washing liquids are for example carbonates and hydrogen carbonates of the alkaline and alkaline earth metals as well as ammonia in the form of the aqueous solution. A 3% sodium carbonate solution in water is particularly preferred.

It is then optionally possible to wash the reaction solution with an acid solution.

Acid washing is advantageous to remove unreacted basic portions of the reaction solution, in particular when methylene chloride is used as the solvent.

The washing solution consists of a mixture of water and alcohols. Mixtures of aliphatically saturated alcohols which contain 1 to 4 carbon atoms are preferably used, an acid substance also optionally being present. The mixing ratio water:alcohol may for example be between 5 and 0.5, preferably 1–3 (V/V).

Acid substances that may be considered for the washing liquid are for example mineral acids and organic acids, for example hydrochloric acid, sulphuric acid or tartaric acid, and citric acid. A 10% solution of hydrochloric acid in water is particularly preferred.

The mixture is then washed once again with a mixture of water and alcohols. Mixtures of aliphatic saturated alcohols which contain 1 to 4 carbon atoms are preferably used, it also being possible for a basic substance to be optionally present.

The mixing ratio water:alcohol may for example be between 5 and 0.5, preferably 1–3.

The washed phases are then combined and dried in conventional manner and the solvent is then removed (preferably under reduced pressure, for example 5–100 mbar) optionally after addition of 1.5–3 liters, preferably 2–2.5 liters of an aliphatic alcohol (related to 1 part by weight of dried product). Alcohols that may for example be used are saturated aliphatic alcohols with a chain length of 1 and 5 carbon atoms. The particularly preferred alcohol here is n-butanol, isopropanol. The purpose of this alcohol treatment is to remove the residual water completely.

The product so-obtained can be purified in the conventional manner (e.g. by chromatography, recrystallization).

An alkylphosphocholine crude product or the solid residue as described above is for example suspended in a saturated aliphatic ketone (3–6 carbon atoms), for example acetone, butanone, methyl-tert.-butylketone, stirred for 1 to 4 hours, preferably 2 hours, suction filtered and dried at 20° C. to 50° C. in a vacuum at 5 Torr to 100 Torr.

The purification process can be performed in a solvent selected from the group consisting of anhydrous alcohols with 1 to 5 carbon atoms, water, or any mixtures of said alcohols with or without water. The purification time is about 30 minutes to 48 hours. The temperature of the solution is about 10° C. to the boiling point of the solution.

The following purification process is, however, particularly preferred:

The product which has been prepurified in this manner is taken up in anhydrous alcohols ($C_1$ to $C_4$) or in alcohols which contain not more than up to 5 percent by weight of water at 20° C. to 60° C., preferably 40° C. and insoluble constituents are filtered off.

Alcohols that may for example be used are methanol, ethanol, isopropanol, butanol, isobutanol.

The prepurified product may also be dissolved in water. The filtrate obtained is then stirred with a mixed-bed ion exchanger, for example Amberlite® MB3, for example for 1 to 5 hours, preferably 2 hours at 10° C. to 50° C., preferably 20° C.

Instead of a mixed-bed ion exchanger the purification may also be effected simultaneously or successively with an acid ion exchanger and a basic ion exchanger. Ion exchangers which may also be used are all insoluble solids which contain ion exchanging groups.

Acid ion exchangers are those which contain for example acid groups such as sulphonic acid groups, carboxyl groups. Examples are ion exchangers with sulphonic acid groups in a polystyrene matrix such as Amberlite® IR 120, Dowex® HCR, Duolite® C 20 or Lewatit® S 100.

Weakly acid ion exchangers are for example those which carry carboxylic acid groups on the basis of a polyacrylic acid matrix, such as Amberlite® IRC 76, Duolite® C 433 or Relite® CC.

Basic ion exchangers that may for example be considered are those carrying on a polymer matrix (e.g. polystyrene matrix) primary, secondary, tertiary or quaternary amino groups such as Duolite® A 101, Duolite® A 102, Duolite® 15 A 348, Duolite® A 365, Duolite® A 375, Amberlite® IRA 67, Duolite® A 375, Amberlite® IRA 458 and Duolite® A 132.

Mixed-bed ion exchangers are mixtures of acid and alkaline ion exchanger resins, such as Amberlite® MB1, Amberlite® MB2, Amberlite® MB3 and Amberlite® MB6.

It is also possible to use all conventional ion exchangers in the process.

Reference is also made to Ullmann's Encyclopedia of Industrial Chemistry, 5th Edition (1989), Volume A14, p. 450.

Following vacuum suctioning of the ion exchanger resin the mixture is evaporated under reduced pressure (for example 20 Torr to 200 Torr) at 40° C. to 70° C. and the mixture is then recrystallized from halogenated hydrocarbons or from alcohol/ketone mixtures.

Halogenated hydrocarbons that may for example be considered for the recrystallization are hydrocarbons containing 1 to 6 carbon atoms where one or several or all carbon atoms are replaced by chlorine atoms.

It is for example possible to use methylene chloride, chloroform, ethylene chloride, chlorobenzene.

Alcohols that may be considered are saturated aliphatic alcohols with 1 to 6 carbon atoms and 1 to 2 hydroxyl groups. Ketones that may be considered are saturated, aliphatic ketones with 3 to 8 carbon atoms.

The mixing ratio alcohol:ketone is 1 to 1–5 (volume/volume).

An ethanol/acetone mixture in the ratio of 1:1 (V/V) is particularly preferred.

The crystals of alkylphosphocholine obtained are suction filtered and if necessary washed for example with saturated hydrocarbons containing 1 to 6 carbon atoms. (Temperature of the washing liquid may be for example 15 to 30° C.).

The product may be dried for example in a vacuum at 40° C. to 80° C. over conventional drying agents, for example phosphorus pentoxide or silica gel. The purification level of the whole batch may be subject to in-process control at any time during the purification process by taking an analysis of the samples to determine whether the alkylphosphocholines have reached sufficient purity. If the sample has insufficient purity, either more ion-exchanger may be added to the solution or the reaction time may be increased, or both.

DETAILED DESCRIPTION OF PREFERRED EMBODIMENTS

The following examples illustrate the invention.

EXAMPLE 1

Preparation of hexadecyl phosphocholine 1.0 Moles (92 ml) POCl$_3$ in 1.5l chloroform are added to a 6-liter stirring apparatus under nitrogen and cooled in an ice bath to 5° C. 0.90 Moles (218 g) hexadecanol are dissolved in 700 ml chloroform and added dropwise together 4.00 Moles (320 ml) pyridine at a temperature of 5–12° C. Dropping time: 1.25 hours. The dropping funnel is then flushed with the remaining 300 ml chloroform. After one and half hours post-stirring at 0–5° C., 1.35 Moles (372 g) solid choline tosylate are added and then 400 ml pyridine added dropwise over 15 minutes. This causes the temperature to rise to 20° C. The ice bath is removed and the reaction mixture is stirred at room temperature for 3 hours. For purposes of hydrolysis, 150 ml water are added dropwise over 20 minutes, the temperature rising from 25° C. to 36° C. After stirring for half an hour, the reaction solution is washed in each case once with 1.50 liters water/methanol (1:1), 1.50 liters 3% sodium carbonate/methanol (1:1) and 1.50 liters water/methanol (1:9). The chloroform phase washed in this manner is dried over sodium sulphate and evaporated in a rotary evaporator under a vacuum after addition of 50 ml i-propanol. n-butanol is added for drying and the mixture is evaporated in a rotary evaporator again. Purification is carried out as follows:

The residue is suspended in 2.0 liters acetone, stirred for approx. 2 hours, suction filtered and dried at 30° C. in a vacuum. Raw yield: 325 g (87%). The crude product is taken up in 3.0 liters absolute ethanol and insoluble portions filtered off. The filtrate is stirred for two hours with 1.0 liters mixed-bed ion exchanger Amberlite MB 3® (FLUKA). After suction filtration of the ion exchanger resin, the mixture is evaporated in a rotary evaporator in a vacuum and then recrystallized once from 0.70 liters methylene chloride. Complete crystallization is achieved in the refrigerator. The crystals are suction filtered and washed with pentane. The mixture is then dried in a vacuum at 30° C. over phosphorus pentoxide. Yield 193 g (0.47 Moles, 53%) The reaction product has a melting point of 241–245° C.

The same procedure is used for Examples 2–5.

Example 2:

D-19390:

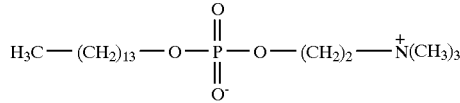

Mp; 260° C. (disintegration)
C$_{19}$H$_{42}$NO$_4$P (379.52)
TL: 89 a (chloroform/methanol/ammonia 25% = 70:20:10)
Rf: 0.27

| EA: | | C | H | N |
|---|---|---|---|---|
| | calc. | 60.13% | 11.16% | 3.69% |
| | .H$_2$O | 57.41% | 11.16% | 3.52% |

|  |  |  |  |  |  |  |  |
|---|---|---|---|---|---|---|---|
| found | C | 57.40% | H | 11.42 | N | 3.61% |  |
|  |  | 57.43% |  | 11.47% |  | 3.65% |  |

$^1$H-NMR: (250 MHz, CDCl$_3$)
σ = 0.90 ppm (t, 3H)  3.80 (q, 2H)
1.25 (m, 22H)  3.85 (m, 2H)
1.55 (p, 2H)  4.25 (m, 2H)
3.40 (liters, 9H)

Example 3:

D-20403:

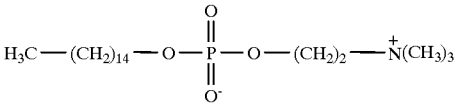

Mp; 244° C. (disintegration)
C$_{20}$H$_{44}$NO$_4$P (393.55)
TL: 89 a (chloroform/methanol/ammonia 25% = 70:40:10)
Rf: 0.49

|  |  |  |  |  |  |  |  |
|---|---|---|---|---|---|---|---|
| EA: | calc. | C | 61.04% | H | 11.27% | N | 3.56% |
|  | .2H$_2$O |  | 55.92% |  | 11.26% |  | 3.26% |
|  | found | C | 56.14% | H | 10.99 | N | 3.76% |
|  |  |  | 55.74% |  | 10.85% |  | 3.59% |

$^1$H-NMR: (250 MHz, CDCl$_3$)
σ = 0.90 ppm (t, 3H)  3.80(q, 2H)
1.30 (m, 24H)  3.85 (m, 2H)
1.55 (p, 2H)  4.25 (m, 2H)
3.40 (liters, 9H)

Example 4:

D-19767:

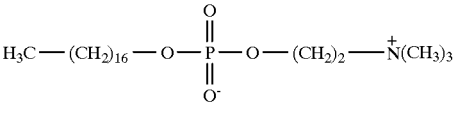

Mp; 254–256° C.
C$_{22}$H$_{48}$NO$_4$P (421.61)
TL: 127 c (I-butanol/glacial acetic acid/water = 60:20:20)
Rf: 0.34

|  |  |  |  |  |  |  |  |
|---|---|---|---|---|---|---|---|
| EA: | calc. | C | 62.68% | H | 11.48% | N | 3.32% |
|  | .H$_2$O |  | 60.11% |  | 11.46% |  | 3.19% |
|  | found | C | 60.2% | H | 11.7 | N | 3.1% |
|  |  |  | 60.5% |  | 11.7% |  |  |

$^1$H-NMR: (250 MHz, CDCl$_3$)
σ = 0.90 ppm (t, 3H)  3.80 (q, 2H)
1.25 (m, 28H)  3.85 (m, 2H)
1.60 (p, 2H)  4.25 (m, 2H)
3.40 (liters, 9H)

Example 5:

D-19391:

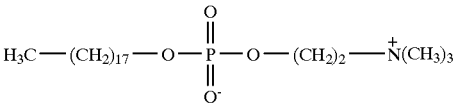

Mp; 258° C. (disintegration)
C$_{23}$H$_{50}$NO$_4$P (435.62)
TL: 126 (I-butanol/glacial acetic acid/water = 40:10:10)
Rf: 0.13

|  |  |  |  |  |  |  |  |
|---|---|---|---|---|---|---|---|
| EA: | calc. | C | 63.41% | H | 11.57% | N | 3.22% |
|  | .H$_2$O |  | 60.90% |  | 11.55% |  | 3.09% |
|  | found | C | 60.80% | H | 11.93 | N | 3.15% |
|  |  |  | 60.83% |  | 12.02% |  | 3.15% |

$^1$H-NMR: (250 MHz, CDCl$_3$)
σ = 0.90 ppm (t, 3H)  3.80(q, 2H)
1.25 (m, 30H)  3.85 (m, 2H)
1.60 (p, 2H)  4.30 (m, 2H)
3.40 (liters, 9H)

what is claimed is:

1. A purification process for alkylphosphocholines comprising:

to a solution of an alkylphosphocholine prepared by a process comprising:

reacting an n-alkanol having a chain length of C$_{14}$–C$_{18}$ with phosphorus oxychloride in a single vessel:

reacting the product obtained, without isolation and purification, in an inert solvent with a choline salt in the presence of a basic substance, to form a corresponding phosphoric acid diester chloride; and hydrolyzing the phoophoric acid diester chloride to obtain the desired product, which is taken up in a solvent selected from the group consisting of anhydrous alcohols with 1 to 5 carbon atoms, water, and any mixtures of said alcohols with or without water, thereby obtaining the solution of the alkylphosphocholine;

adding a mixed bed ion-exchanger or successively or simultaneously at least one ion-exchanger selected from the group consisting of an acid ion-exchanger and a basic ion-exchanger;

stirring the solution and the ion-exchanger together;

separating the solution from the ion-exchanger;

optionally sampling and analyzing the solution at any time during the purification process for determining purification level; and recovering purified alkylphosphocholine.

2. A process according to claim 1, comprising reacting the n-alkanol having a chain length of C$_{14}$–C$_{18}$ with the phosphorus oxychloride in the presence of an inert solvent.

3. A process according to claim 1, comprising reacting the n-alkanol having a chain length of C$_{14}$–C$_{18}$ with the phosphorus oxychloride in the absence of a solvent.

4. A process according to claim 1, comprising reacting the n-alkanol having a chain length of C$_{14}$–C$_{18}$ with the phosphorus oxychloride in the presence of a basic substance.

5. A process according to claim 1, comprising reacting the n-alkanol having a chain length of C$_{14}$–C$_{18}$ with the phosphorus oxychloride in the absence of a basic substance.

6. A process for the preparation of C$_{14}$–C$_{18}$ alkylphosphocholines according to claim 1, wherein reaction temperature is 0° C. to 40° C.

7. A purification process according to claim 1, wherein purification time is about from 30 minutes to 48 hours.

8. A purification process according to claim 1, wherein temperature of the solution is about from 10° C. to boiling point of the solution.

9. A purification process for alkylphosphocholines comprising:

adding to a solution of an alkylphosphocholine in a solvent selected from the group consisting of anhydrous alcohols with 1 to 5 carbon atoms, water, and any mixture of said alcohols with or without water, a mixed-bed ion-exchanger or successively or simultaneously, at least one ion-exchanger selected from the group consisting of an acid ion-exchanger and a basic ion-exchanger;

stirring the solution and the ion-exchanger together:

separating the solution from the ion-exchanger; and optionally sampling and analyzing the solution at any time during the purification process for determining purification level; and recovering purified alkylphosphoclioline.

10. A purification process according to claim 9, wherein purification time is about from 30 minutes to 48 hours.

11. A purification process according to claim 9, wherein temperature of the solution is about from 10C to boiling point of the solution.

* * * * *